(12) United States Patent
Joo et al.

(10) Patent No.: US 10,723,693 B2
(45) Date of Patent: Jul. 28, 2020

(54) METHOD FOR PREPARING BENZOIC ACID AMIDE COMPOUND

(71) Applicant: AMOREPACIFIC CORPORATION, Seoul (KR)

(72) Inventors: Yung Hyup Joo, Yongin-si (KR); Heung Soo Baek, Yongin-si (KR); Yong Jin Kim, Yongin-si (KR); Hong-Ju Shin, Yongin-si (KR); John Hwan Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/736,406

(22) PCT Filed: Jun. 3, 2016

(86) PCT No.: PCT/KR2016/005914
§ 371 (c)(1),
(2) Date: Dec. 14, 2017

(87) PCT Pub. No.: WO2017/003107
PCT Pub. Date: Jan. 5, 2017

(65) Prior Publication Data
US 2018/0179146 A1 Jun. 28, 2018

(30) Foreign Application Priority Data

Jun. 30, 2015 (KR) .................. 10-2015-0092704
May 31, 2016 (KR) .................. 10-2016-0067409

(51) Int. Cl.
*C07C 231/02* (2006.01)
*C07C 213/02* (2006.01)
*C07C 249/08* (2006.01)

(52) U.S. Cl.
CPC .......... *C07C 231/02* (2013.01); *C07C 213/02* (2013.01); *C07C 249/08* (2013.01); *C07C 2603/74* (2017.05)

(58) Field of Classification Search
None
See application file for complete search history.

(56) References Cited

U.S. PATENT DOCUMENTS

| 9,254,251 | B2 | 2/2016 | Joo et al. |
| 2008/0280989 | A1 | 11/2008 | Kim et al. |
| 2014/0234241 | A1* | 8/2014 | Joo .................. A61K 8/42 424/62 |

FOREIGN PATENT DOCUMENTS

| CN | 104370793 | A | | 2/2015 |
| EP | 2740721 | A2 | | 6/2014 |
| JP | 2009504726 | A | | 2/2009 |
| JP | 2014529583 | A | | 11/2014 |
| KR | 100286421 | B1 | | 4/2001 |
| KR | 100502833 | B1 | | 7/2005 |
| KR | 20070046577 | | * | 5/2007 |
| KR | 20070046577 | A | | 5/2007 |
| KR | 20130004616 | | * | 1/2013 |
| KR | 20130004616 | A | | 1/2013 |
| KR | 20130015954 | A | | 2/2013 |
| WO | WO-2013022236 | A2 | * | 2/2013 ............... A61K 8/42 |

OTHER PUBLICATIONS

Wikipedia page for "dichloromethane", downloaded from https://en.wikipedia.org/wiki/Dichloromethane on Mar. 2, 2020 (Year: 2020).*
Baek et al., "Adamantyl N-benzylbenzamide: New series of depigmentation agents with tyrosinase inhibitory activity", Bioorganic & Medicinal Chemistry Letters, 2012, vol. 22, pp. 2110-2113.
Chapsal et al., "Catalytic asymmetric transformations with fine-tunable biphenol-based monodentate ligands", Tetrahedron: Asymmetry, 2006, vol. 17, pp. 642-657.
International Search Report for International Application No. PCT/KR2016/005914 (2 Pages) (dated Sep. 6, 2016).
Jin Cai et al., "Discovery of phenoxybutanoic acid derivatives as potent endothelin antagonists with antihypertensive activity", Bioorganic & Medicinal Chemistry, vol. 23, No. 4, Feb. 1, 2015, pp. 657-667.
Kang Kyung Ho et al., "Solution-phase combinatorial synthesis of isoxazolines and isoxazoles using [2+3] cycloaddition reaction of nitrile oxides", Tetrahedron Letters, vol. 42, No. 6, 2001, pp. 1057-1060.
Mohamed Ali Ayedi et al., "Synthesis of Primary Amines by One-Pot Reductive Amination of Aldehydes", Synthetic Communications, vol. 43, No. 16, Aug. 18, 2013, pp. 2127-2133.
The extended European Search Report, Application No. 16818140.2, dated May 9, 2018.
"2,4-dimethoxybenzoic acid, d=1.2481 g/ml", Chemical Book, 2017, (https://www.chemicalbook.com/ChemicalProductProperty_EN_CB4363756.htm).
"2,4-Dihydroxybenzoic acid", ChemSrc, 2020,(https://www.chemsrc.com/en/cas/89-86-1_1188194.html).
"4-hydroxybenzoic acid, d=1.46 g/ml", Wikipedia, 2020, (https://en.wikipedia.org/wiki/4-Hydroxybenzoic_acid).
"1-adamantanol, d=0.854"4", Chemical Book, 2017, (https://www.chemicalbook.comChemicalProductProperty_EN_cb2135047.htm).

* cited by examiner

*Primary Examiner* — Amy C Bonaparte
(74) *Attorney, Agent, or Firm* — Lucas & Mercanti, LLP

(57) ABSTRACT

The present invention relates to a method for preparing a benzoic acid amide compound in a high yield by presenting a novel method for preparing a benzyl amine compound to be used as a reactant and delimiting the reaction condition of each step by using the same, and the method is economically advantageous since mass production is possible.

7 Claims, No Drawings

METHOD FOR PREPARING BENZOIC ACID AMIDE COMPOUND

CROSS-REFERENCE TO RELATED APPLICATIONS

This application is a 371 of PCT/KR2016/005914, filed on Jun. 3, 2016 which claims the benefit of Korean Patent Application No. 10-2015-0092704, filed Jun. 30, 2015 and Korean Patent Application No. 10-2016-0067409, filed May 31, 2016 the contents of each of which are incorporated herein by reference.

TECHNICAL FIELD

The present invention relates to a method for preparing a benzoic acid amide compound suitable for mass production.

BACKGROUND ART

5-Adamantane-1-yl-N-(2,4-dihydroxybenzyl)-2,4-dimethoxy-benzoic acid amide is one of compounds having an adamantine group as a substituent, and is presented as an active ingredient of a cosmetic composition because it has an excellent whitening effect by inhibiting melanin existing in the outer layer of the human skin.

Regarding to preparation of the above compound, in Korean Patent Publication No. 2013-0015954, the compound is prepared according to the following Reaction Formula.

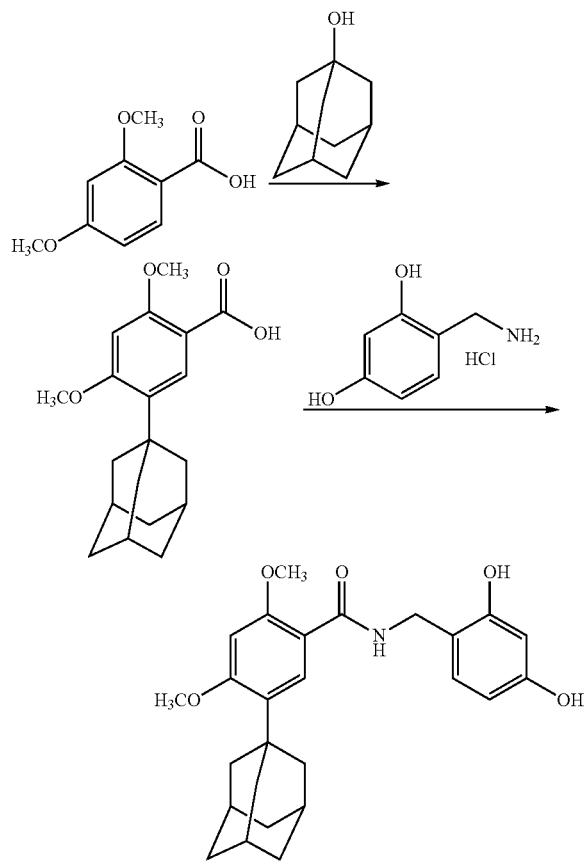

Specifically, 5-adamantane-1-yl-N-(2,4-dihydroxybenzyl)-2,4-dimethoxy-benzoic acid amide is prepared through the steps of: (i) reacting 2,4-dihydroxy benzoic acid and 1-adamantanol in dichloromethane as a solvent at room temperature in the presence of acetic acid and sulfuric acid as a catalyst to synthesize 5-adamantanyl-2,4-dihydroxy benzoic acid; (ii) reacting the 5-adamantanyl-2,4-dihydroxy benzoic acid and dimethyl sulfate in the presence of sodium hydroxide or potassium hydroxide to synthesize 5-adamantanyl-2,4-dimethoxy benzoic acid; and (iii) reacting the 5-adamantanyl-2,4-dimethoxy benzoic acid with benzyl amine in the presence of N-hydroxy succinimide and N,N'-dicyclohexyl carbodiimide.

In this preparing method, when the acetic acid and the solvent used for preparing the 5-adamantanyl-2,4-dihydroxy benzoic acid of the step (i) are consumed 8 times or more and 2 times or more, respectively, compared to the reactant, the reaction time is required at least 5 hours, and a yield is about 80 to 85%.

Further, in the step (iii), a coupling agent for coupling, for example, N-hydroxy succinimide/1,3-dicyclohexyl carbodiimide (HOSu/DCC), $SOCl_2$ or 1-ethyl-3-(3-dimethyl aminopropyl)carbodiimide (EDC) in dichloromethane, cyanuric chloride in MeCN, $B(OH)_3$ in toluene and the like, is used under expensive water/dioxane solvent, and accordingly, the solvent is limitedly required. The yield of the compound thus obtained is very low as about 30%, and the purity is also low due to a complex mixture remained in the final product.

In particular, dihydroxy benzyl amine to be used as a reactant in the step (iii) is prepared through the following steps.

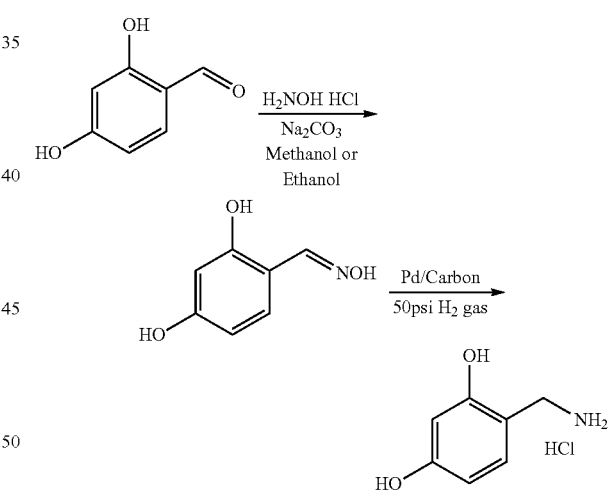

In the above reaction, dihydroxy benzaldehyde as a starting material is reacted with sodium carbonate in methanol or ethanol for 5 hours for activation, and then hydrochloric acid in methanol or ethanol is added thereto for additional reaction to prepare an oxime compound.

Then, reduction reaction is performed by using high-pressure hydrogen gas in the presence of a catalyst, in which Pd is loaded in a carbon support, to prepare dihydroxy benzyl amine. At this time, the reaction takes a long time about 5 hours, nevertheless it show a yield of about 50%. Moreover, this reaction has problems that it should use expensive Pd, and the process is complicated and process cost is increased because hydrogen gas of 50 psi is used during the reaction.

Also, as process increases in size, there were many problems unsuitable for mass production, for example, a yield decreases, irregular production pattern is form or separation of a mixture becomes impossible.

Thus, there are many restrictions on industrial application of the benzoic acid amide compound in spite of it excellent effect related to whitening. Therefore, it is needed to develop a novel preparation method with improved production efficiency.

PRIOR ART DOCUMENT (Patent Document 1) Korean Patent Publication No. 2013-0015954, "Novel benzoic acid amide compound"

DETAILED DESCRIPTION OF THE INVENTION

Technical Problem

Accordingly, the present inventors had been continuing research for presenting a novel method for preparing a benzoic acid amide compound. As a result, by specifying reaction conditions of each process, the process time which is required for entire preparation can be reduced, an economic advantage can be secured because of not using expensive materials and catalysts, and the benzoic acid amide compound can be prepared in a high yield.

Moreover, the dihydroxy benzyl amine to be used as a reactant can be prepared in a high yield of 90% or more in an aqueous solution without an organic solvent in a short time, and the compound is used for preparing the benzoic acid amide compound.

Accordingly, an object of the present invention is to provide a method for preparing a benzoic acid amide compound which can be easily applied to mass production.

Further, another object of the present invention is to provide a method for preparing a benzyl amine compound which can be used as a reactant in preparing the benzoic acid amide compound.

Technical Solution

In order to accomplish the objects described above, provided is a method for preparing a benzoic acid amide derivative of Chemical Formula 1, which is expressed as Reaction Formula 1 and comprises a step of performing an amide coupling reaction of a benzyl amine compound of Chemical Formula 2 and an adamantanyl benzoic anhydride of Chemical Formula 3 under a base catalyst:

[Reaction Formula 1]

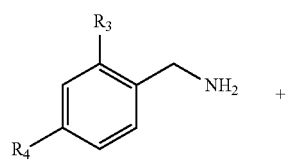

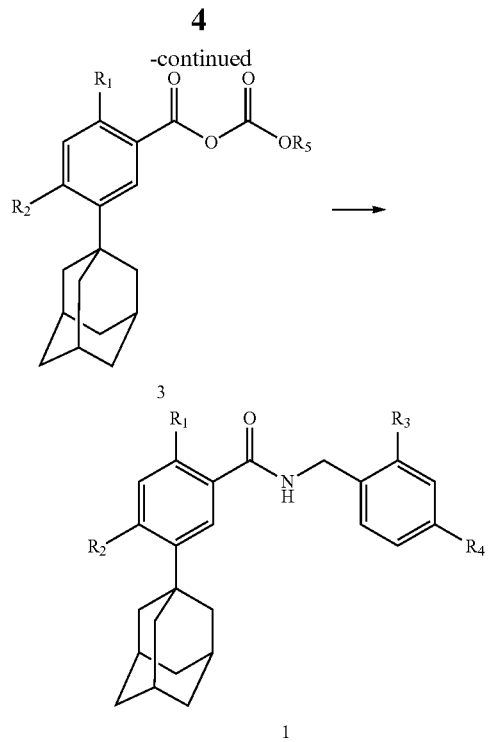

(wherein, $R_1$ to $R_5$ have the same meanings as defined in the specification)

At this time, as expressed in the following Reaction Formula 2, the benzyl amine compound of Chemical Formula 2 is prepared through the following steps of:

T1) preparing a benzaldehyde oxime compound of Chemical Formula 5 by reacting a benzaldehyde compound of Chemical Formula 4 and hydroxyl amine in an aqueous alkaline solution; and T2) treating the benzaldehyde oxime compound of Chemical Formula 5 with a reducing agent in an aqueous acidic solution:

[Reaction Formula 2]

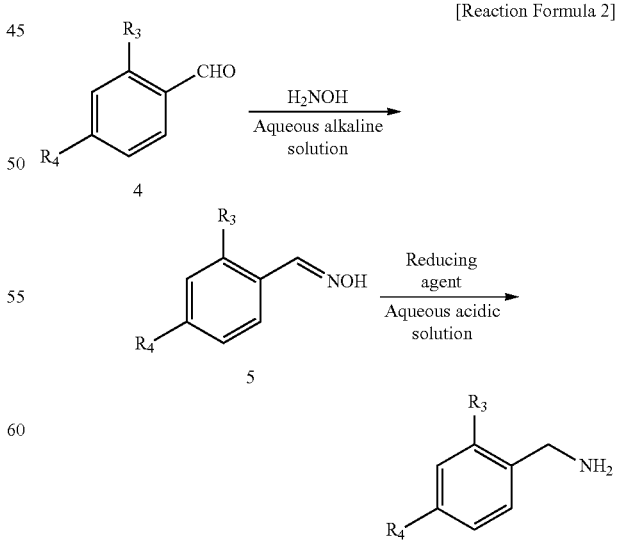

(wherein, $R_3$ and $R_4$ have the same meanings as defined in the specification)

Advantageous Effect

The method for preparing a benzoic acid amide compound presented in the present invention can reduce the cost by reducing the entire reaction time and also can prepare the compound in a high yield.

Further, the present invention presents a method which can prepare a key intermediate, benzyl amine derivative, in an aqueous solution without an organic solvent in a short time in a high yield of 90% or more.

Thus, according to the present invention, mass production of the benzoic acid amide compound can be realized in a short time in a high yield.

Mode for the Invention

Hereinafter, the present invention will be described in more detail.

The present invention presents a novel method for preparing a benzoic acid amide derivative, which has excellent effects in the field of organic chemistry field, cosmetics and the like, in particular, an excellent whitening effect by inhibiting melanin.

Specifically, the benzoic acid amide derivative is expressed as the following Chemical Formula 1:

[Chemical Formula 1]

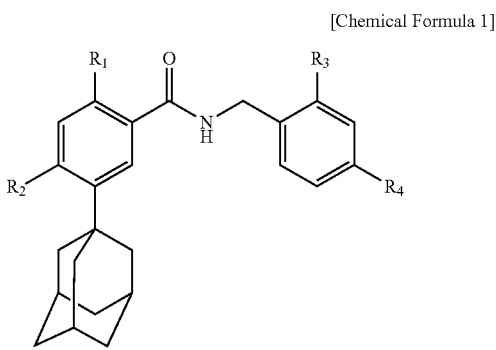

(wherein,
$R_1$ to $R_4$ are the same or different, and are each independently hydrogen, a hydroxyl group, a $C_1$ to $C_5$ alkoxyl group, a $C_3$ to $C_6$ cycloalkoxyl group, a $C_6$ to $C_{20}$ aryloxy group or a $C_1$ to $C_5$ haloalkoxyl group).

The alkoxyl group mentioned herein may be linear chain or branched chain, and it is preferred to have carbon number of 1 to 5. For example, it may be methoxy, ethoxy, n-propoxy, isopropoxy, i-propyloxy, n-butoxy, isobutoxy, tert-butoxy, sec-butoxy, 1,2-dimethylbutoxy and the like, but not limited thereto.

The cycloalkoxyl group mentioned herein may be ring chain, and it is preferred to have carbon number of 3 to 6. For example, it may be cyclopropoxy, cyclobutoxy, cyclopentoxy or cyclohexyloxy and the like, but not limited thereto.

The aryloxy group mentioned herein may preferably have carbon number of 6 to 20. For example, it may be phenoxy, p-toryloxy, m-toryloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy and the like, but not limited thereto.

The haloalkoxyl group mentioned herein means an alkoxyl group substituted with a halogen group (—F, —Cl, —Br or —I).

The alkyl group mentioned herein may be linear chain or branched chain, and it is preferred to have carbon number of 1 to 6. For example, it may be methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl and the like, but not limited thereto.

Preferably, $R_1$, $R_3$ and $R_4$ are the same or different, and each independently any one selected from the group consisting of hydrogen, a hydroxyl group and a $C_1$ to $C_3$ alkoxyl group.

More preferably, the benzoic acid amide derivative of Chemical Formula 1 may be selected from the following compounds: (1) 5-adamantane-1-yl-2,4-dihydroxy-N-[2-(4-hydroxyphenyl)-ethyl]-benzoic acid amide; (2) 5-adamantane-1-yl-2-hydroxy-N-[2-(4-hydroxyphenyl)-ethyl]-4-methoxy-benzoic acid amide; (3) 5-adamantane-1-yl-N-[2-(4-hydroxyphenyl)-ethyl]-2,4-dimethoxy-benzoic acid amide; (4) 5-adamantane-1-yl-N-(2,4-dihydroxybenzyl)-2,4-dihydroxy-benzoic acid amide; (5) 5-adamantane-1-yl-N-(2,4-dihydroxybenzyl)-2-hydroxy-4-methoxy-benzoic acid amide; (6) 5-adamantane-1-yl-N-(2,4-dihydroxybenzyl)-2,4-dimethoxy-benzoic acid amide; (7) 3-adamantane-1-yl-4-hydroxy-N-[2-(4-hydroxyphenyl)-ethyl]-benzoic acid amide; (8) 3-adamantane-1-yl-N-[2-(4-hydroxyphenyl)-ethyl]-4-methoxy-benzoic acid amide; (9) 3-adamantane-1-yl-N-(2,4-dihydroxybenzyl)-4-hydroxy-benzoic acid amide; and (10) 3-adamantane-1-yl-N-(2,4-dihydroxybenzyl)-4-methoxy-benzoic acid amide.

Among the compound, it may preferably be 5-adamantane-1-yl-N-(2,4-dihydroxybenzyl)-2,4-dimethoxy-benzoic acid amide.

The benzoic acid amide derivative of Chemical Formula 1 may have excellent melanin formation inhibitory effect and tyrosinase activity hindering effect because absorption power is enhanced by increased lipophilicity of the adamantine group. There may be other many other effects besides the above effects.

Specifically, as shown in the following Reaction Formula 1, the benzoic acid amide derivative of Chemical Formula 1 is prepared by a method comprising a step of performing an amide coupling reaction of a benzyl amine compound of Chemical Formula 2 and an adamantanyl benzoic anhydride of Chemical Formula 3 under a base catalyst:

[Reaction Formula 1]

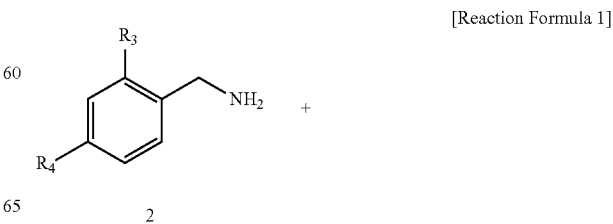

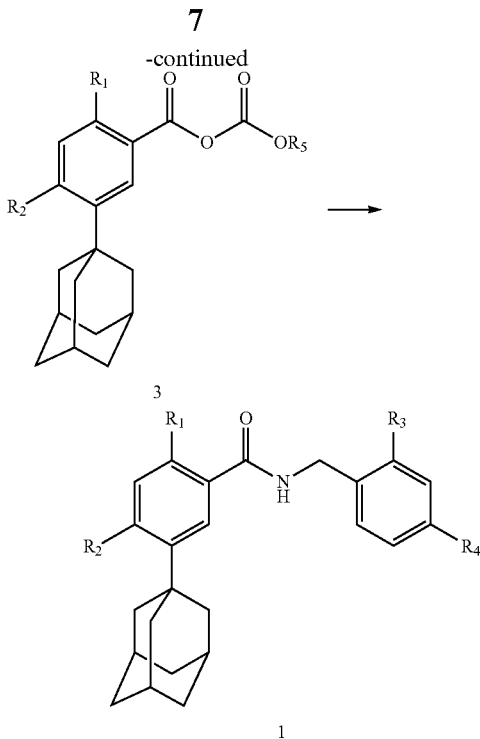

(wherein, $R_1$ to $R_4$ have the same meanings as defined above, and $R_5$ is a $C_1$ to $C_6$ alkyl group).

According to the Reaction Formula 1, the amide coupling reaction is performed in a solvent under a base catalyst.

At this time, the base catalyst to be used is not particularly limited in the present invention, and it may be any base catalyst known in the art. Specifically, the base catalyst may be any one selected from the group consisting of triethyl amine, pyridine, N,N-diisopropyl amine, N-methyl morpholine and a combination thereof, and it may preferably be triethyl amine.

The solvent may be any one selected from the group consisting of dichloromethane, chloroform, 1,2-dichloroethane, 1,1,2-trichloroethane, chlorobenzene and a combination thereof.

This reaction is performed at 0 to 40° C., more preferably at room temperature, and performed preferably for 30 min to 4 hours, more preferably 2 to 3 hours.

As mentioned earlier, the amide coupling reaction of Reaction Formula 3 can be performed without a separate coupling agent. According to the reaction described in Korea Patent Publication No. 2013-0015954, a coupling agent that is a combination of specific coupling agent and solvent is used. The final yield of this method is low as about 30% and also it is difficult to separate the product finally obtained. Further, it is unsuitable for mass production process because the used agents are expensive.

However, the coupling reaction of the present invention can prepare the benzoic acid amide of Chemical Formula 1 compound stably in a high yield of 75 to 95% or more, preferably 75 to 90% or more, compared to the yield of just 30% so far, by reacting the adamantanyl benzoic anhydride of Chemical Formula 3 having a leaving group and the benzyl amine compound of Chemical Formula 2, which can easily react with the compound, without a coupling agent and a specific solvent in relation to the coupling agent. Further, it is easy to separate the benzoic acid amide compound from the final product, and it is possible to perform a process with chip reagents. Accordingly, there is an advantage of cost reduction and great effectiveness on mass production process.

In particular, the benzyl amine compound of Chemical Formula 2 to be used as a reactant in the Reaction Formula 1 is hard to be prepared, its raw material is expensive, and the stability of the material itself is very low. Accordingly, considerable attention is required to apply the compound as a reactant. In particular, like the compound of Chemical Formula 2, a compound in which $R_3$ and $R_4$ is substituted at position 3,4 or 2,5, not 2,4 is cheaper and more stable than a compound in which $R_3$ and $R_4$ is substituted at position 2,4.

Further, in the past, the benzyl amine compound is prepared by reacting a benzaldehyde derivative with sodium acetate in an organic solvent, i.e., ethanol for a long time of 5 hours or longer to prepare an oxime compound and then further reacting in the presence of expensive Pd catalyst. It seems that this method is not suitable for mass production in terms of time, cost and yield.

Accordingly, the present invention presents a novel method for preparing the benzyl amine compound of Chemical Formula 2 to solve the problems (i.e., stability, price, time and yield) of the 2,4-substituted compound.

Preferably, the benzyl amine compound of Chemical Formula 2 can be prepared according to the following Reaction Formula 2:

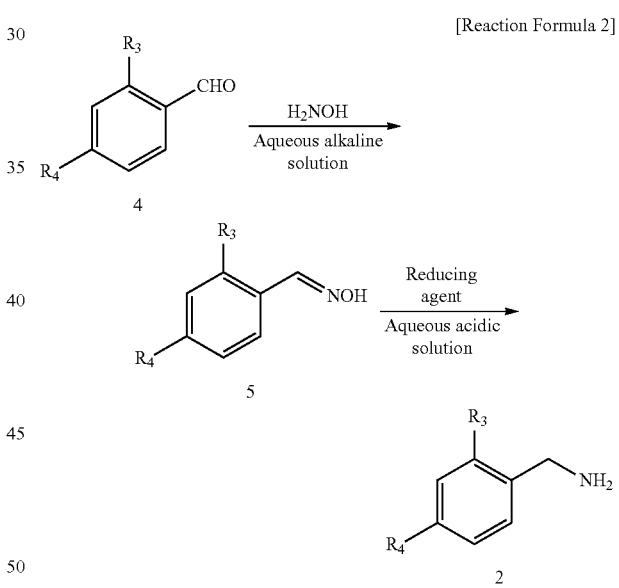

(wherein, $R_3$ and $R_4$ have the same meanings as defined above).

Specifically, according to the Reaction Formula 2, the benzyl amine compound of Chemical Formula 2 is prepared through the steps of:

T1) preparing a benzaldehyde oxime compound of Chemical Formula 5 by reacting a benzaldehyde compound of Chemical Formula 4 and hydroxyl amine in an aqueous alkaline solution; and T2) treating the benzaldehyde oxime compound of Chemical Formula 5 with a reducing agent in an aqueous acidic solution.

In the step T1), the benzaldehyde compound of Chemical Formula 4 used as a starting material may be any compound if satisfying $R_3$ and $R_4$, for example 2,4-dihydroxy benzaldehyde. This compound can be directly prepared or purchased from the market. The benzaldehyde compound is not dissolved well in water, but it can be easily reacted under the basic condition.

The reaction of the step T1) is performed in an aqueous solution in the presence of base.

At this time, the base may be any one selected from the group consisting of sodium carbonate, sodium bicarbonate, potassium carbonate and potassium bicarbonate, and it may preferably be sodium carbonate. The base may be used at molar ratio of 1:0.01 to 1:1 based on the amount of the starting material of Chemical Formula 8.

The reaction is performed at 0 to 40° C., more preferably at room temperature, and performed preferably for 30 min to 3 hours, more preferably 1 to 2 hours. When crystals are precipitated after the reaction, the benzaldehyde oxime compound of Chemical Formula 5 can be obtained by filtration.

In the preparation of the benzaldehyde oxime compound, the reaction time can be largely reduced to 1 to 2 hours, and also the benzaldehyde oxime compound of Chemical Formula 5 can be obtained in a high yield of 95% or more, compared to the conventional method reacting sodium acetated with an organic solvent, ethanol, for a long time of 5 hours or more.

Then, the step T2) is performed in an aqueous solution in the presence of acid and a reducing agent.

The acid may be any one selected from the group consisting of hydrochloric acid, sulfuric acid and a combination thereof, and it may preferably be hydrochloric acid. The acid may be used at molar ratio of 1:1 to 1:10 based on the amount of the starting material of Chemical Formula 5.

At this time, the reducing agent used in the step T2) may be zinc, preferably zinc powder, and it converts the oxime to amine.

The zinc powder is inexpensive and also easy to buy. Thus, the cost can be reduced economically when mass producing the benzyl amine compound. At this time, the zinc powder is purchased from the market, and used at molar ratio of 1:1 to 1:10 based on the amount of the compound of Chemical Formula 5.

The reaction is performed at −4 to 40° C., and performed preferably for 30 min to 4 hours, more preferably 2 to 3 hours. The reaction can prepare the benzyl amine compound of Chemical Formula 2 in a high yield.

In the past, a precious metal catalyst, Pd, was used in the step T2) as a reducing agent, and in this case, there were problems of increase of the production cost and the reaction time, and also a problem of deterioration of the reproducibility due to irregular yield from 50 to 95%. In particular, during a mass production process, there were problems that many by-products were formed, the yield was reduced to 50% or less, or it was difficult to separate the product as the form of intact hydrochloride or acetate.

Accordingly, as mentioned earlier, the present invention can reduce the cost by using inexpensive zinc powder as a reducing agent and also largely reduce the reaction time. Further it can secure a yield of 90 to 95% when applied to a mass production process. In addition, because the reaction can be proceeded in an aqueous solution, working conditions can be improved compared to the conventional methods using an organic solvent.

The benzyl amine compound of Chemical Formula 2 finally obtained is prepared in the form of a salt due to addition of acid, and after washing thereof, or after simple filtration thereof without a separate purification followed by removal of the solvent, it can be applied as a reactant of the Reaction Formula 1 in the form of amine hydrochloride.

Further, the adamantanyl benzoic anhydride of Chemical Formula 3 reacted with the benzyl amine compound of Chemical Formula 2 in the Reaction Formula 1 can be prepared according to the following Reaction Formula 3:

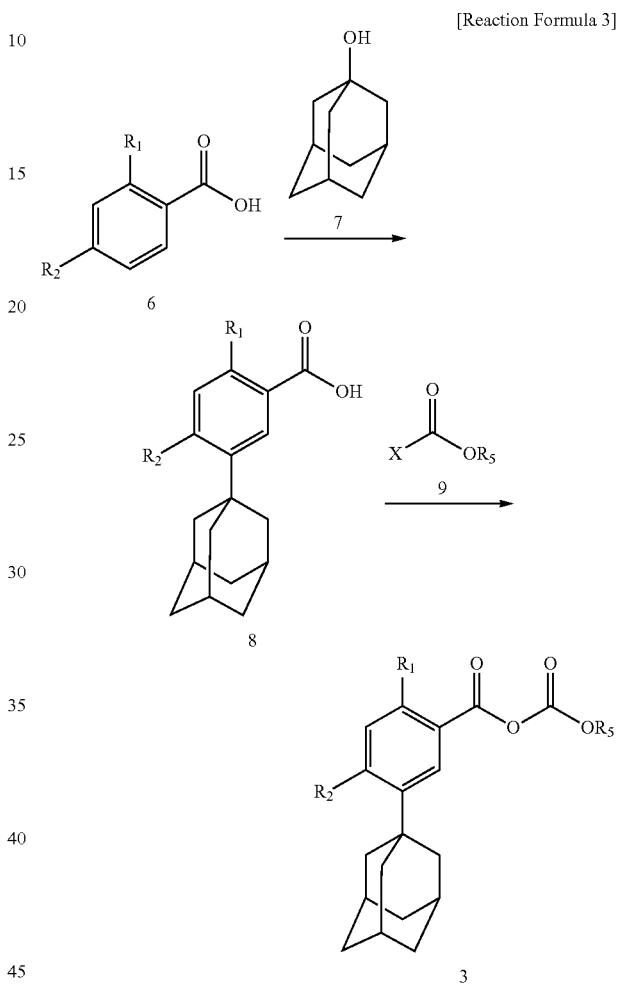

(wherein $R_1$, $R_2$, $R_4$, $R_5$ have the same meanings as defined above and X is halogen atom).

According to the Reaction Formula 3, the adamantanyl benzoic anhydride of Chemical Formula 3 is prepared through the following steps of:

S1) performing adamantylation of a benzoic acid compound of Chemical Formula 6 and 1-adamantanol of Chemical Formula 7 under an acid catalyst to prepare an adamantanyl benzoic acid compound of Chemical Formula 8; and S2) reacting an adamantanyl benzoic acid compound of Chemical Formula 8 and alkyl haloformate of Chemical Formula 9 in the presence of a base catalyst.

First, in the step S1), the benzoic acid compound of Chemical Formula 6 and the 1-adamantanol of Chemical Formula 7 are reacted.

The benzoic acid compound of Chemical Formula 6 used as a starting material is a benzoic acid derivative substituted with carboxylic acid on its benzene ring, and a specific compound may be any compound satisfying $R_1$ and $R_2$ mentioned in the compound of Chemical Formula 1. For example, the benzoic acid compound of Chemical Formula 6 may be 2,4-dihydroxy benzoic acid, 2-hydroxy-4-methoxybenzoic acid, 2,4-dimethoxybenzoic acid, 4-hydroxybenzoic acid or 4-methoxybenzoic acid, and it may be directly prepared or purchased from the market.

The 1-adamantanol of Chemical Formula 7 can be directly prepared or purchased from the market.

The benzoic acid compound of Chemical Formula 6 and the 1-adamantanol of Chemical Formula 7 can be reacted considering stoichiometric equivalence ratio, and the reaction is performed at molar ratio of 1:1 to 1:1.2. If the molar ratio of the 1-adamantanol is excessive, the reaction may occur at a undesirable position.

This reaction is performed in a solvent in the presence of an acid catalyst.

The acid catalyst is to increase the reaction rate, and may be any one selected from the group consisting of hydrochloric acid, sulfuric acid, trifluoroacetic acid, acetic acid and a combination thereof, and it may preferably be a mixture of trifluoroacetic acid and sulfuric acid.

At this time, the solvent may be dichloromethane.

The amount of the solvent is not limited if the amount is enough to proceed the reaction. However, in order to reduce the cost by using the solvent, the solvent is used within the optimum range, preferably at volume ratio (reactant:solvent) of 1:1 to 1:50, more preferably 1:1 to 1:30. At this time, the reactant means the sum of the benzoic acid compound and the 1-adamantanol.

The reaction temperature and the reaction time is controlled to allow that the reaction is sufficiently conducted, the compound is prepared in a high yield, and the time required to prepare the final benzoic acid amide compound from the starting material is reduced.

Specifically, the step S1) is performed within the reflux temperature of the solvent, preferably for 30 min to 2 hours, more preferably for 1 to 1.5 hours. If the reaction temperature is low, the reaction rate may be slow, and if the temperature is too high, degradation may occur. Further, the reaction time is time required for sufficient reaction of the Reaction Formula 2. If the time is exceeded, there is a concern that the total process time required for preparing the benzoic acid amide compound may be extended. Therefore, the reaction is performed within the above time.

In particular, in the case of the step S1), in the conventional method, the reaction is performed in the presence of an excessive amount of sulfuric acid and acetic acid together with an organic solvent for a long time of 5 hours or more. Therefore, there is a problem that a yield is low even after the reaction for a long time.

However, the present invention has advantages that the reaction can be proceeded even though the amount of the organic solvent is reduced to ½ or less and the amount of the acid (e.g., acetic acid) is reduced to ⅛ or less, and the reaction time is largely reduced to up to 2 hour, compared to the conventional time. Such reduction of the amount of the solvent used and the process time is advantageous to increase the productivity of the entire process and also to reduce the process cost. In particular, because it is possible to obtain a yield of about 90% or more, the present invention is also advantageous in terms of the reaction efficiency.

Then, in the step S2), the adamantanyl benzoic acid compound of Chemical Formula 8 and the alkyl haloformate of Chemical Formula 9 are reacted to prepare the adamantanyl benzoic anhydride of Chemical Formula 3.

The alkyl haloformate of Chemical Formula 9 is used as a leaving group, and the reaction of the adamantanyl benzoic acid compound of Chemical Formula 8 and the benzyl amine compound of Chemical Formula 2 is not directly occurred. Thus, in order to activate the reaction, the alkyl haloformate converts the adamantanyl benzoic acid compound of Chemical Formula 8 to an anhydride having excellent reactivity.

The anhydride is in the form of a mixed anhydride, and has an advantage that the anhydride is easily reacted with the benzyl amine compound of Chemical Formula 2.

The alkyl haloformate for preparing the anhydride may be any compound satisfying the above mentioned $R_5$ and X, and it may preferably be ethyl chloroformate or isobutyl chloroformate, which is directly prepared or purchased from the market.

The adamantanyl benzoic acid derivative of Chemical Formula 8 and the alkyl haloformate can be prepared considering stoichiometric equivalence ratio, and the reaction is performed at molar ratio of 1:1 to 1:1.2. If the molar ratio of the alkyl haloformate is excessive, the reaction may occur at a undesirable position.

This reaction may be performed in a solvent under a base catalyst.

The base catalyst, which can be used, may be at least one selected from the group consisting of triethyl amine, pyridine, N,N-diisopropyl amine, N-methyl morpholine and a combination thereof, and it may preferably be triethyl amine.

At this time, the solvent may preferably be dichloromethane.

The reaction may be performed at low temperature, preferably −4 to 0° C., and it is preferred to be performed for 10 min to 2 hours.

The steps mentioned above are summarized in the following Reaction Formula 6.

[Reaction Formula 4]

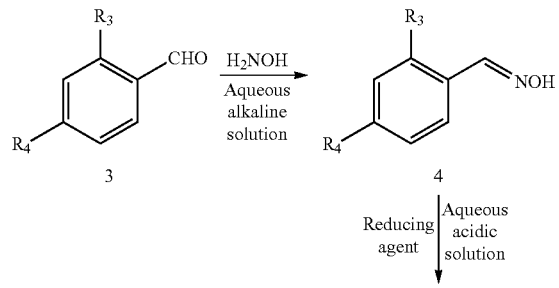

-continued

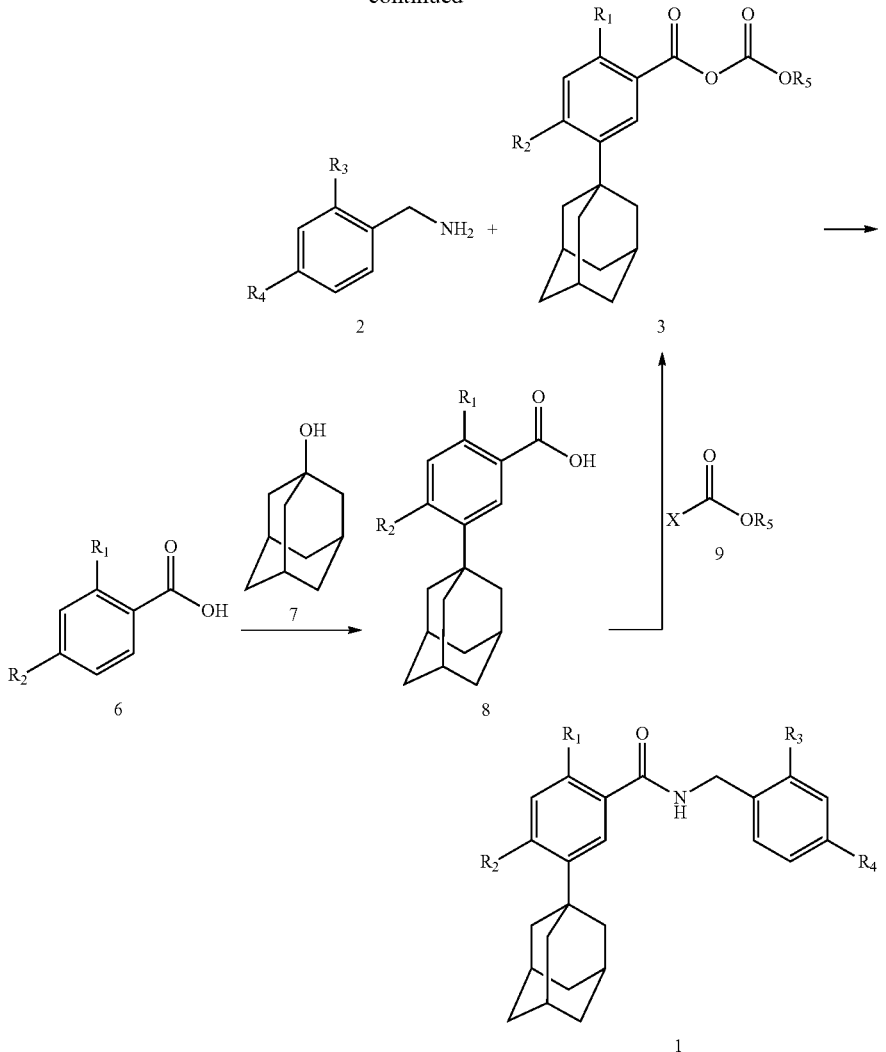

(wherein, $R_1$ to $R_5$ and X have the same meanings as defined above)

The method for preparing the benzoic acid amide of Chemical Formula 1 according to the present invention as shown in the Reaction Formula 4 presents process conditions required for the reaction of the benzyl amine compound of Chemical Formula 2 and the adamantanyl benzoic anhydride of Chemical Formula 3, and a novel condition for preparing the compound of Chemical Formula 2. Therefore, the method is suitable for mass production.

First, advantages of the novel method for preparing a benzyl amine compound of Chemical Formula 2 are as follows.

First, preparation of the compound of Chemical Formula 4 is proceeded in an aqueous solution, the reaction time is short (within a maximum of 2 hours), and the compound can be prepared in a high yield of 95% or more. Accordingly, it can be found that this method is an improved method, compared to the conventional method in which the reaction is proceeded in an organic solvent for 5 hours or more but the yield is low.

And, the compound of Chemical Formula 2 can be prepared in a high yield of up to about 95% after reaction within a maximum of 3 hours by using inexpensive zinc powder. This method can solve the problems of the conventional method such as a long reaction time and unstable yield from 50 to 95% even though using an expensive reducing agent, Pd.

As a result, it can be found that the method for preparing the benzyl amine compound of Chemical Formula 2 is very improved on the process efficiency such as process time and the process cost, compared to the conventional method.

Further, regarding to the preparation of the adamantanyl benzoic anhydride of Chemical Formula 3, the compound of Chemical Formula 8 prepared by using the compound of Chemical Formula 6 as a starting material largely reduces the amount of the solvent and the acid consumed during the preparation and also reduces the process time to a maximum of 2 hours, but it can secure a yield of about 90%.

Moreover, by going through the form of the compound of Chemical Formula 3, the reaction for preparing the compound of Chemical Formula 1 can be easily proceeded, the benzoic acid amide of Chemical Formula 1 compound can be prepared in a high yield of 75% or more, and after completing the reaction, the desired compound can be easily separated with inexpensive reagents. It can be found that this method is very improved, compared to the conventional method which has problems that expensive catalyst and reagents are used, the product is obtained in a low yield of about 30%, and it is difficult to separate the desired compound.

Consequently, the method for preparing the benzoic acid amide derivative of Chemical Formula 1 of the present invention as shown in the Reaction Formula 4 can prepare a desired compound in a high yield and in a short time, reagents to be used in each step can be replaced with inexpensive reagents, and also the amount of the reagents can be reduced. Further, the method has an advantage that it can produce a desired compound due to its high reproducibility and reaction stability.

Thus, the preparing method according to the present invention can preferably be applied to a mass production process of the benzoic acid amide derivative of Chemical Formula 1.

The benzoic acid amide compound of Chemical Formula 1 thus prepared by this method has a whitening effect. Thus, it can be used to a cosmetic composition and any other fields.

For example, due to its skin whitening effect, it is useful as an ingredient of an external preparation for the skin, in particular, whitening cosmetic products. The final product to be contained in the external preparation for the skin may be in the form of at least one of the compound, its isomers, its pharmaceutically acceptable salts, its pro-drugs, its hydrates and its solvates.

BEST MODE FOR CARRYING OUT THE INVENTION

Hereinafter, the preferred embodiment of the present invention will be described in detail based on examples. However, the embodiments of the present invention may be modified in various ways, and the scope of the present invention should not be interpreted as being limited to the examples. The embodiments of the present invention are provided just for explaining the present invention more perfectly to those having ordinary skill in the art.

Preparative Example 1: Preparation of 2,4-dihydroxy benzyl amine

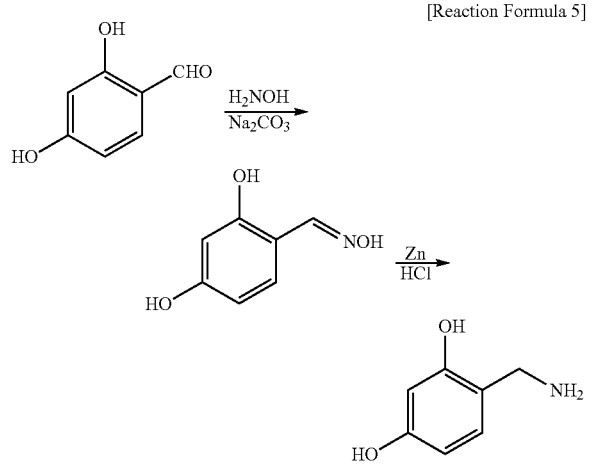

[Reaction Formula 5]

While mixing and stirring 2,4-dihydroxybenzaldehyde (50 g) and water (600 mL), hydroxyl amine hydrochloride (32.7 g) was dropped. The mixture was stirred at room temperature for 1 hour while slowly dropping 0.23 M aqueous sodium carbonate solution (200 mL) to the mixture. After the starting materials were completely disappeared, the solid formed in the reaction solution was filtered and washed with water to obtain 2,4-dihydroxy benzaldehyde oxime (54 g, yield 97%).

$^1$H-NMR (300 MHz, DMSO-$d_6$) 10.9 (brs, 1H), 10.05 (brs, 1H), 9.76 (brs, 1H), 8.19 (s, 1H), 7.23 (d, 1H), 6.30 (s, 1H), 6.28 (s, 1H)

The 2,4-dihydroxybenzaldehyde oxime (5.5 g) thus obtained was put into a new flask and 6M hydrochloric acid solution (48 ml) was added thereto. Then, zinc powder (9.42 g) was slowly dropped while stirring the resulting solution under ice cooling. At first, the solution in the reaction vessel was stirred to maintain the temperature in the reaction vessel to 40° C. or less while dropping the zinc powder a little at a time. After completely adding the zinc, whether the starting material was disappeared or not was checked while stirring the resulting solution at room temperature for 2 hours. Then the excessive zinc was removed by filtration, and the remained solution was concentrated under a reduced pressure to remove water. Finally, 2,4-dihydroxybenzyl amine was obtained in the form of hydrochloride.

The prepared 2,4-dihydroxy benzyl amine (5.5 g, yield 90%) was obtained in the form of solid hydrochloride, and used at the next reaction without separate purification.

EXAMPLE 1

Preparation of 5-adamantane-1-yl-N-(2,4-dihydroxy benzyl)-2,4-dimethoxy-benzoic acid amide According to the following reaction, the title compound was prepared.

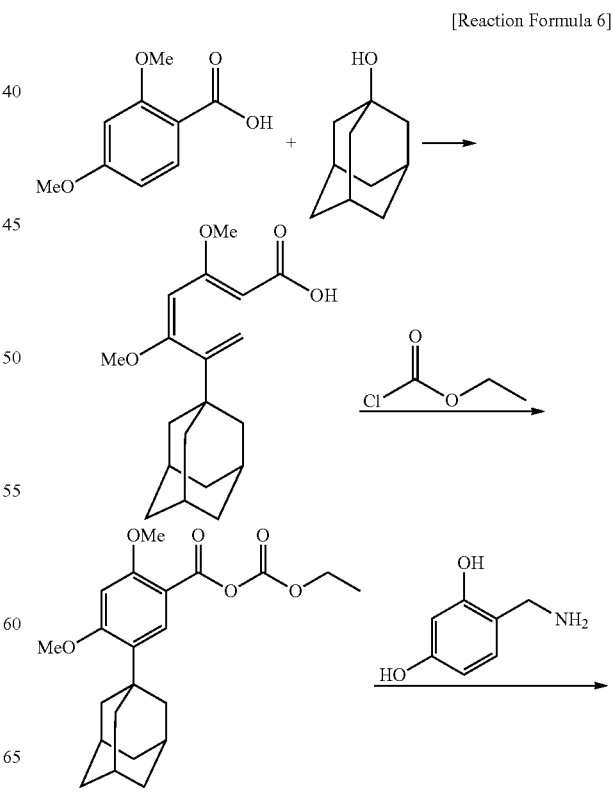

[Reaction Formula 6]

-continued

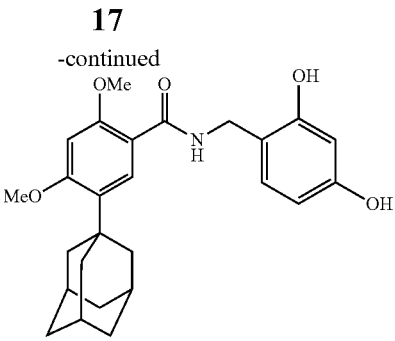

(1) Preparation of 5-adamantane-1-yl-2,4-dimethoxybenzoic acid

While dissolving 2,4-dimethoxybenzoic acid (10 g) and 1-adamantanol (9.2 g) in dichloromethane (120 mL) and stirring the resulting solution, trifluoroacetic acid (4 mL) and concentrated sulfuric acid (6.7 mL) were dropped thereto, and then refluxed for 2 hours. The stirred mixture solution was distilled under reduced pressure. The residue was dissolved in ethanol (100 mL) and water (100 mL) and stirred, and then pH of the solution was adjusted to 6 by using 50% potassium hydroxide solution. The solid thus formed was filtered, and ethanol (30 mL) and 1N hydrochloric acid solution (120 mL) were added thereto followed by stirring thereof for 1 hour. The solid thus formed was filtered to obtain 5-adamantane-1-yl-2,4-dimethoxybenzoic acid (17 g, yield 97%).

$^1$H-NMR (300 MHz, DMSO-d$_6$) 12.07 (brs, 1H), 7.57 (s, 1H), 6.63 (s, 1H), 3.89 (s, 3H), 3.84 (s, 3H), 1.99 (s, 9H), 1.71 (s, 6H).

(2) Preparation of 5-adamantane-1-yl-2,4-dimethoxybenzoic acid anhydrous salt In order to process the 5-adamantane-1-yl-2,4-dimethoxybenzoic acid (9.1 g) prepared in the above (1) in the form of a mixed anhydride, the compound was dissolved in dichloromethane (50 mL), triethyl amine (4.8 ml) was added thereto under ice cooling, ethyl chloroformate (3.3 mL) was dropped thereto, and then the resulting solution was stirred for 30 min. When using the formed compound later, the amine hydrochloride was removed by filtration and only the remained solution was used.

(3) Preparation of 5-adamantane-1-yl-N(2,4-dihydroxy benzyl)-2,4-dimethoxy-benzoic acid amide The 2,4-dihydroxy benzyl amine hydrochloride prepared in Preparative Example 1 was dissolved in N,N'-dimethyl formamide (50 ml), and then triethyl amine (4.8 ml) was added thereto. The resulting solution was stirred for 5 min.

While stirring the resulting solution, the 5-adamantane-1-yl-2,4-dimethoxybenzoic acid anhydride solution obtained in the above (2) was dropped thereto. At this time, the temperature in the reaction vessel was maintained to 25° C. or less. Then, the resulting solution was stirred at room temperature for 2 hours.

After completing the reaction, the reacted solution was diluted by adding dichloromethane (50 mL) and extracted with water (100 ml). Again, the organic layer was washed with 1N aqueous hydrochloric acid solution, saturated sodium bicarbonate solution and excess salt water. The organic layer was collected and dried with activated clay and anhydrous magnesium. The solution mixture was filtered and concentrated under a reduced pressure, and then recrystallized with dichloromethane and hexane to obtain the desired compound, 5-adamantane-1-yl-N(2,4-dihydroxy benzyl)-2,4-dimethoxy-benzoic acid amide (9.45 g, yield 75%), as white solid.

$^1$H-NMR (300 MHz, DMSO-d6) 9.67 (s, 1H), 9.13 (s, 1H), 8.51 (m, 1H), 7.78 (m, 1H), 6.92 (d, 1H, J=8.1 Hz), 6.66 (s, 1H), 6.27 (s, 1H), 6.16 (d, 1H, J=8.1 Hz), 4.30 (d, 2H, J=5.4 Hz), 3.93 (s, 3H), 3.88 (s, 3H), 1.98 (s, 9H), 1.71 (s, 6H).

Comparative Example 1

Preparation of 5-adamantane-1-yl-N(2,4-dihydroxy benzyl)-2,4-dimethoxy-benzoic acid amide According to the method described in Korean Patent Publication No. 2013-00159954, the same title compound with Example 1 was prepared.

EXAMPLE 2

Preparation of 5-adamantane-1-yl-N-(2,4-dihydroxybenzyl)-2,4-dihydroxy-benzoic acid amide The procedure of Example 1 was repeated except for using 2,4-dihydroxybenzoic acid instead of 2,4-dimethoxybenzoic acid as a starting material to prepare the title compound.

[Reaction Formula 7]

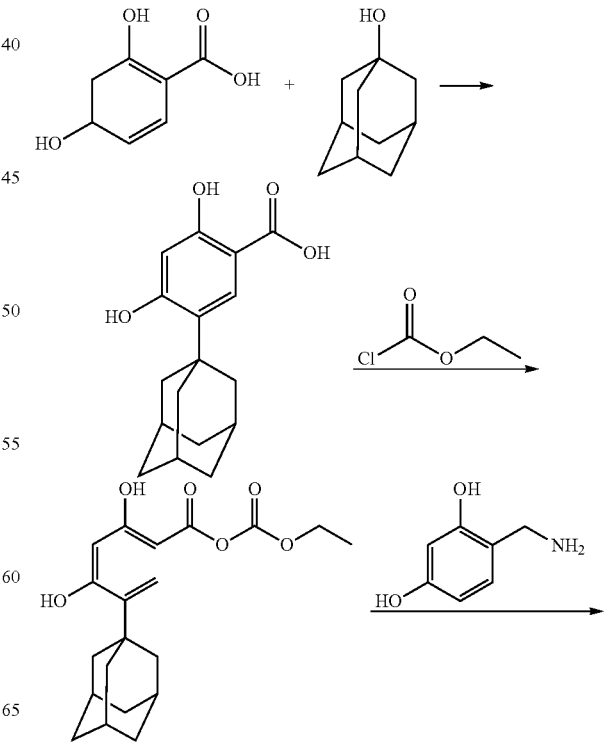

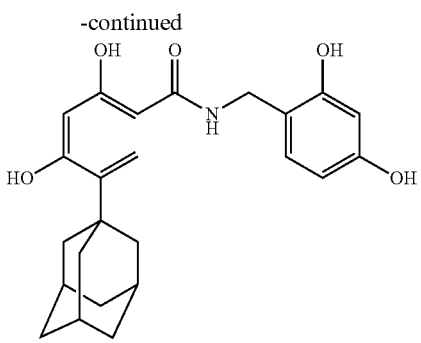

¹H-NMR (300 MHz, DMSO-d6) 12.41 (s, 1H), 9.91 (s, 1H), 9.40 (s, 1H), 9.09 (s, 1H), 8.83 (m, 1H), 7.47 (s, 1H), 6.89 (d, 1H, J=8.1 Hz), 6.26 (s, 2H), 6.16 (d, 1H, J=8.1 Hz), 4.29 (m, 2H), 2.02 (s, 9H), 1.70 (s, 6H).

EXAMPLE 3

Preparation of 5-adamantane-1-yl-N-(2,4-dihydroxybenzyl)-2-hydroxy-4-methoxy-benzoic acid amide The procedure of Example 1 was repeated except for using 2-hydroxy-4-methoxybenzoic acid instead of 2,4-dimethoxybenzoic acid as a starting material to prepared the title compound.

[Reaction Formula 8]

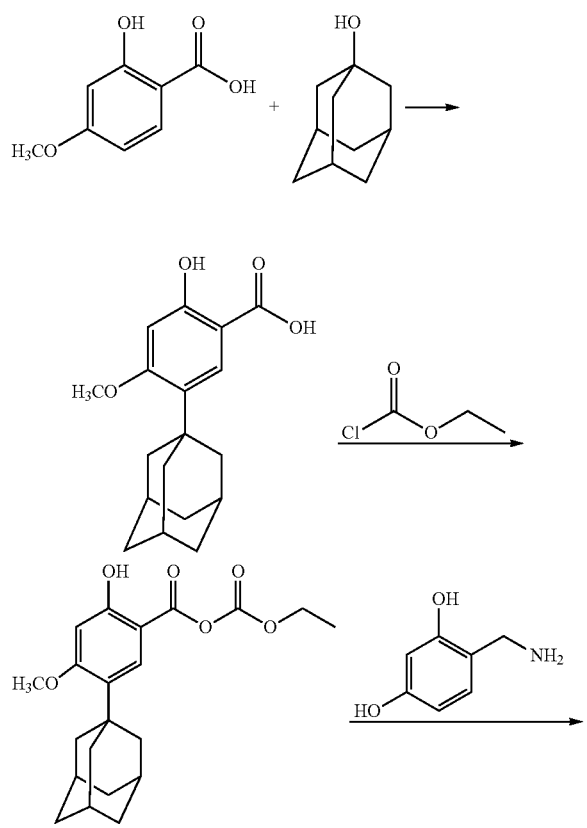

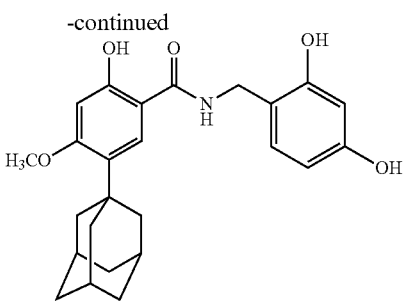

¹H-NMR (300 MHz, DMSO-d6) 12.73 (s, 1H), 9.40 (s, 1H), 9.11 (s, 1H), 8.95 (m, 1H), 7.52 (s, 1H), 6.90 (d, 1H, J=8.4 Hz), 6.43 (s, 1H), 6.28 (s, 1H), 6.17 (d, 1H, J=8.4 Hz), 4.31 (d, 2H, J=5.4 Hz), 3.79 (s, 3H), 2.00 (s, 9H), 1.71 (s, 6H).

Text Example 1: Comparison of Reaction Time and Yield

Reaction time required for preparing the compounds of Example 1 and Comparative Example 1 and yield were measured and the results are shown in the following Table 1. At this time, the reaction time was calculated with only the time required for the reaction except for the time required for the post processing.

TABLE 1

|  | Comparative Example 1 | Example 1 |
|---|---|---|
| Total reaction time (hour) | 24 hours | 4.5 hours |
| Yield (%) | 45% | 75% |

As shown in the results in the Table 1 about Comparative Example 1 and Example 1, it can be found that, in the case of Example 1, the time required for preparing the same compound was largely reduced and the yield was largely increased.

From this result, it can be found that the method for preparing benzoic acid amide presented in the present invention can preferably be applied to a mass production process because the method can reduce the entire process time and also can prepared the compound in a high yield.

What is claimed is:

1. A method for preparing a benzoic acid amide derivative of Chemical Formula 1, which is expressed as Reaction Formula 1 and 3 below, and comprises steps of the following S1) to S3):

S1) performing reaction of adamantylation of a benzoic acid compound of Chemical Formula 6 and 1-adamantanol of Chemical Formula 7 under trifluoroacetic acid and concentrated sulfuric acid as an acid catalyst in dichloromethane within the reflux temperature of the dichloromethane to prepare an adamantanyl benzoic acid compound of Chemical Formula 8;

S2) reacting the adamantanyl benzoic acid compound of Chemical Formula 8 and an alkyl haloformate of Chemical Formula 9 in the presence of a base catalyst to prepare an adamantanyl benzoic anhydride of Chemical Formula 3; and S3) performing an amide coupling reaction of a benzyl amine compound of Chemical Formula 2 or a hydrochloride salt thereof and the adamantanyl benzoic anhydride of Chemical Formula 3 under a base catalyst:

[Reaction Formula 1]

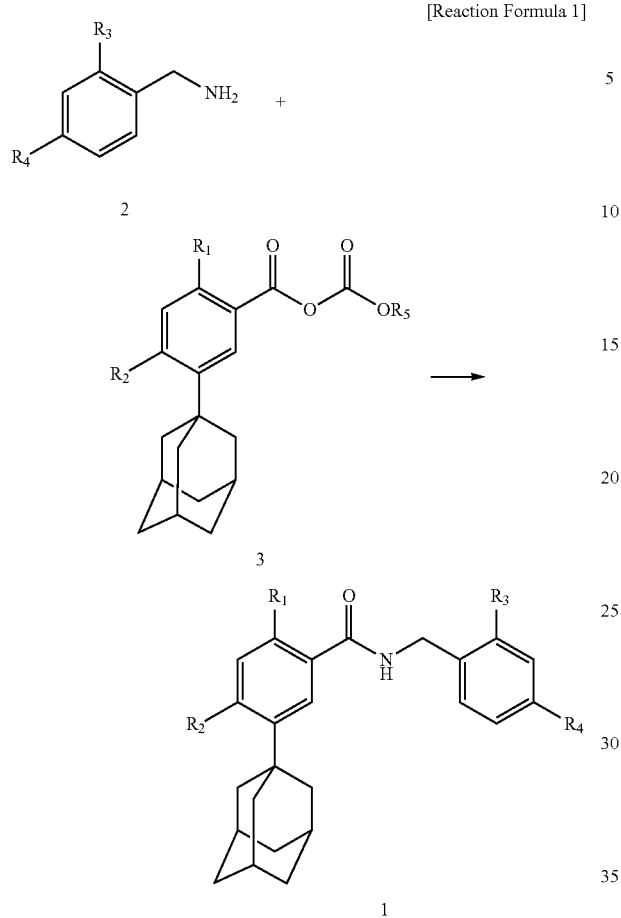

[Reaction Formula 3]

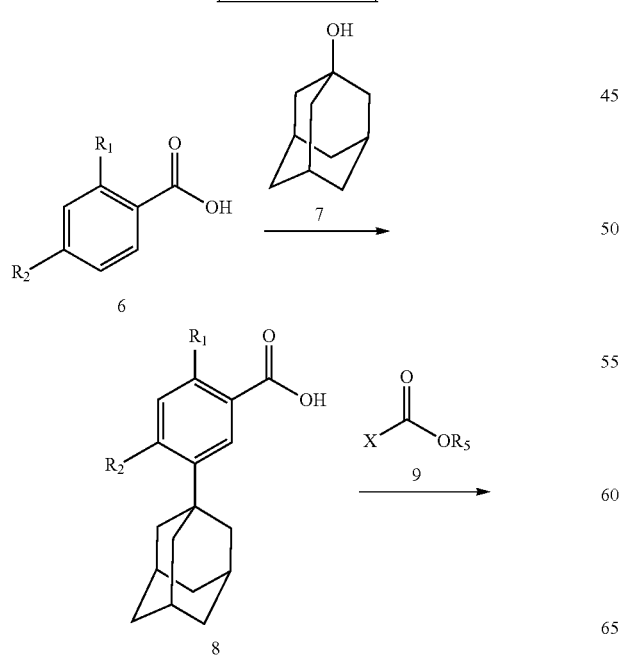

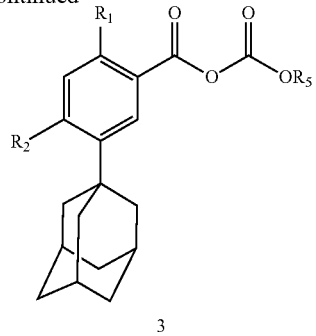

wherein,
- a reaction time of the step S1) is 30 min to 2 hours and a yield of the adamantanyl benzoic acid compound of Chemical Formula 8 in the step S1) is 95% or more,
- a volume ratio in the step S1) of dichloromethane to reactant consisting of the benzoic acid compound of Chemical Formula 6 and the 1-adamantanol of Chemical Formula 7 is 1:1 to 7:1,
- a yield of the benzoic acid amide derivative of Chemical Formula 1 is 75% or more based on the benzyl amine compound of Chemical Formula 2,
- $R_1$ and $R_2$ are methoxy group,
- $R_3$ and $R_4$ are the same or different, and are each independently hydrogen, a hydroxyl group, a $C_1$ to $C_5$ alkoxyl group, a $C_3$ to $C_6$ cycloalkoxyl group, a $C_6$ to $C_{20}$ aryloxy group or a $C_1$ to $C_5$ haloalkoxyl group,
- $R_5$ is a $C_1$ to $C_6$ alkyl group, and
- X is halogen atom, wherein the benzyl amine compound of Chemical Formula 2 is prepared by steps T1) and T2, expressed as Reaction Formula 2:
- T1) preparing a benzaldehyde oxime compound of Chemical Formula 5 by reacting a benzaldehyde compound of Chemical Formula 4 and hydroxyl amine in an aqueous alkaline solution; and
- T2) treating the benzaldehyde oxime compound of Chemical Formula 5 with a reducing agent in an aqueous acidic solution:

[Reaction Formula 2]

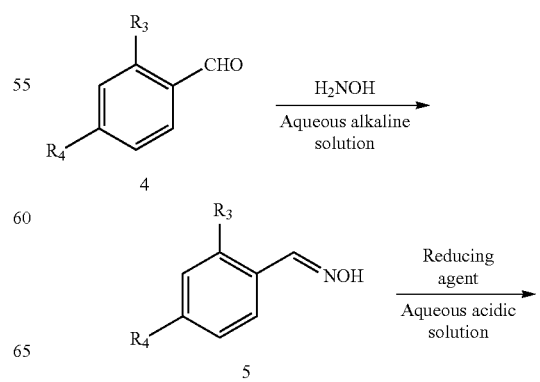

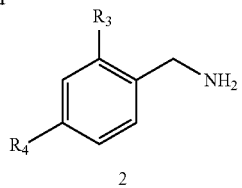

wherein, $R_3$ and $R_4$ are the same or different, and are each independently hydrogen, a hydroxyl group, a $C_1$ to $C_5$ alkoxyl group, a $C_3$ to $C_6$ cycloalkoxyl group, a $C_6$ to $C_{20}$ aryloxy group, or a $C_1$ to $C_5$ haloalkoxyl group.

2. The method for preparing a benzoic acid amide derivative of claim 1, wherein the $R_3$ and $R_4$ are a hydroxyl group.

3. The method for preparing a benzoic acid amide derivative of claim 1, wherein the base catalyst of S3) is any one selected from the group consisting of triethyl amine, pyridine, N,N-diisopropyl amine, N-methyl morpholine and a combination thereof, and the base catalyst of S2) step is any one selected from the group consisting of triethyl amine, pyridine, N,N-diisopropyl amine, N-methyl morpholine and a combination thereof.

4. The method for preparing a benzoic acid amide derivative of claim 1, wherein the amide coupling reaction is performed under at least one solvent selected from the group consisting of dichloromethane, chloroform, 1,2-dichloroethane, 1,1,2-trichloroethane, chlorobenzene and a combination thereof.

5. The method for preparing a benzoic acid amide derivative of claim 1, wherein the aqueous alkaline solution in the T1) step comprises at least one base selected from the group consisting of sodium carbonate, sodium bicarbonate, potassium carbonate, potassium bicarbonate and a combination thereof.

6. The method for preparing a benzoic acid amide derivative of claim 1, wherein the reducing agent in the T2) step is zinc.

7. The method for preparing a benzoic acid amide derivative of claim 1, wherein the aqueous acidic solution in the T2) step comprises hydrochloric acid.

* * * * *